United States Patent [19]

Mallasz

[11] Patent Number: 4,755,384
[45] Date of Patent: Jul. 5, 1988

[54] EXTERNALLY APPLIED ANTISPASMATIC PRODUCTS

[75] Inventor: Otto Mallasz, Budapest, Hungary

[73] Assignee: Központi Valto- es Hitelbank RT, Innovacious Alap, Budapest, Hungary

[21] Appl. No.: 589,894

[22] Filed: Mar. 15, 1984

[30] Foreign Application Priority Data

Jul. 16, 1982 [HU] Hungary .............................. 2312/82

[51] Int. Cl.$^4$ ...................... A61K 33/00; A61L 15/03; C09K 5/00
[52] U.S. Cl. ..................................... 424/131; 424/443; 424/444; 424/445; 424/446; 424/447; 424/448; 424/449; 514/906; 514/947
[58] Field of Search ................... 424/28, 131, 443–449; 514/906, 947

[56] References Cited

U.S. PATENT DOCUMENTS

| 2,111,912 | 3/1938 | Govett | 424/131 |
|---|---|---|---|
| 3,326,213 | 6/1967 | Gallagher | 424/131 |
| 3,464,413 | 9/1969 | Goldfarb et al. | 424/447 |
| 3,598,123 | 8/1971 | Zaffaroni | 424/449 |
| 3,639,575 | 2/1972 | Schmolka | 424/132 |
| 4,340,043 | 7/1982 | Seymour | 604/307 |
| 4,340,590 | 7/1982 | Levitt | 424/132 |

FOREIGN PATENT DOCUMENTS

| 1929722 | 12/1970 | Fed. Rep. of Germany | 424/28 |
|---|---|---|---|
| 2158139 | 6/1973 | France | 424/131 |
| 2465483 | 4/1981 | France | 424/131 |
| 2539032 | 7/1984 | France | 424/28 |
| 58130054 | 8/1981 | Japan | 424/449 |
| 57-28004 | 2/1982 | Japan | 424/28 |
| 57-75913 | 5/1982 | Japan | 424/131 |
| 57-126408 | 8/1982 | Japan | 424/131 |
| 60-60176 | 4/1985 | Japan | 424/28 |
| 2159411 | 12/1985 | United Kingdom | 424/131 |

Primary Examiner—Ronald W. Griffin
Attorney, Agent, or Firm—Horst M. Kasper

[57] ABSTRACT

The invention relates to a process for preparing antispasmatic products which are to be attached to the skin. One or more kinds of metal or metallic substances and/or deficiency and/or trace elements and in a given case the active ingredients of some known pharmaceutical agent is applied to a carrier. The deficiency and/or trace element and in a given case the active ingredient of the known pharmaceutical agent medicament, which are present, are applied in form of a powder, a liquid or in gaseous form. The powdered, liquid and gaseous substances are placed into a recipient, e.g. bag with a permeable wall onto the carrier. Preferably, adhesive strips are provided on the margins of the carrier, while the substances on the carrier are covered with a removable protective layer. If required, the carrier is pretreated with a weak base or acid prior to the application thereof.

29 Claims, No Drawings

EXTERNALLY APPLIED ANTISPASMATIC PRODUCTS

CROSS-REFERENCE TO RELATED APPLICATIONS

This application is a continuation-in-part application of another application filed July 15, 1983 and bearing application Ser. No. PCT/HU83/00040. This claim is made under Section 35 U.S.C. 365 (c), under Section 35 U.S.C. 371 and under any other Section of the U.S.C. supporting such claim.

BACKGROUND OF THE INVENTION

1. Field of the Invention

The invention relates to a process for the preparation of antispasmatic products to be fixed on the skin, in particular for the spasm of the muscles.

2. Brief Description of the Background of the Invention Including Prior Art

It is a well known fact that the bases of the functioning of living creatures including the functioning of the human body are controlled by several phenomena associated with electricity, electrochemistry and chemistry. These phenomina include the currents of cerebral and nerve-activities, the electrolytic and osmotic currents, the diffusion and other, up-to-now not completely and fully understood biological processes, which take place between the cells. An example of such a little understood process is acupuncture. It is also known that several deseases are caused by a deficiency and/or an absence of chemical elements or trace elements. Medical science introduces such deficiency elements into the human body by using different methods. However, no uniform methods are employed. In case of the majority of said methods the patient is confined to bed or other longlasting therapeutical treatments are necessary and all require the presence and supervision of the physician.

SUMMARY OF THE INVENTION

1. Purposes of the Invention

It is an object of the present invention to provide a simple device being suitable for treatment, which can be performed by the patient himself.

It is another object of the invention to provide a method for changing locally the electrolytical balance at the surface of the human body in order to provide for a healing and/or pain removal in local areas.

It is a further object of the present invention to provide a pharmaceutical product which can be applied with an adhesive tape to the outside of the body and which can relieve pain and itching based on metal interaction with the body surface.

These and other objects and advantages of the present invention will become evident from the description which follows.

2. Brief Description of the Invention

The present invention provides a method for producing pharmaceutical skin contacting products, which comprises preparing a carrier for supporting material containing an active metal ingredient, disposing a material containing an active metal ingredient at the carrier, and furnishing an attachment mechanism for bringing the material containing an active metal ingredient into close contact with the skin of the human body.

The carrier can be a member of the group consisting of clay, mud, cream, paste, plaster, dressing, jelly, cotton, gauze, sponge, napkin, pad, bandage, adhesive tape, adhesive and mixtures, providing that the upper layer of the active ingredients contacting the skin should be pure metallic thereof. The active metal ingredient can be provided by a non-toxic member of the group consisting of metal powder, metal filings, wires, fibers, metal fabric, metal strips, metal platelets, metal crystals, metal sponge, metal grain amorphous metal alloy and mixtures thereof. The material containing an active metal ingredient can comprise an element of the group consisting of sulphur, bismuth, radium, tellurium, iodine, arsenic, antimony and mixtures thereof.

The active metal ingredient preferably contains a member of the group consisting of noble metals, copper, zinc, tin, manganese, cobalt, molybdenum, iron alloys thereof and mixtures thereof. A fluid medium can be applied to the carrier via a permeable bag containing said fluid medium. The pharmaceutical skin contacting product can be applied to human skin based on an adhesive support area mechanically adhering to the skin. The active metallic ingredient can be employed in an amount of from about 0.01 to 5.0 gram per square decimeter of the carrier. Before applying on the skin the carrier can be pretreated with an electrolyte generating an aqueous solution with a pH in the range of from about 5 to 9.

There is also provided a pharmaceutical skin contacting product which comprises a material containing an active metal ingredient, a carrier for supporting material containing the active metal ingredient, and means for attaching the carrier supporting an active metal ingredient to the skin of the human body for providing close contact between the active metal ingredient and the skin.

The means for attaching can comprise a surgical adhesive tape with a coating of an acrylate adhesive. The active metal ingredient can be embedded in a carrier containing vinyl plastic. The metal can be copper and the carrier can comprise an adhesive tape where the edge zones around the copper material are provided with an adhesive coating for attachment to the human skin.

There is further provided a process for preparing antispasmatic products, to be fixed on the skin, which comprises applying a substance of the group consisting of metal, metallic substances, deficiency material, trace element and mixtures thereof onto some carrier surface wherein the substance is applied in the form of a member of the group consisting of powder, liquid, gas and/or mixtures thereof, providing on the margins of the carrier an adhesive strip, and covering the substances on the carrier with a removable protective layer.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying examples.

DESCRIPTION OF INVENTION AND PREFERRED EMBODIMENT

In particular, the present invention provides a process by the aid of which one or more metals or metallic substances and/or deficiency elements and/or trace elements are applied onto a carrier being fixed onto the skin, or are mixed with mud, which elements originate very weak currents when put on the surface of the skin, with the aid of the perspiration formed under a plaster or adhesive tape, with perspiration acts like as an electrolyte. The ions of the substance used penetrate during the course of the application into a certain depth of the human organism through the surface of the skin and in particular through the pores. Such penetration can stop the spasm of the muscles in a short time and the deficiency and/or trace elements provided are to promote the recovery over shorter or longer periods.

The substance to be applied onto the carrier can be a solid matter, a liquid or a gas; in case a liquid or gaseous matter is contained, it is to be arranged in a recipient with a permable wall, e.g. in a bag.

In accordance with the invention the product may be produced continuously, e.g. in form of a band and can be cut to pieces later to the size required, or it can be prepared in any configuration, as individual pieces.

By using the process according to the invention, a therapeutical product is produced to be placed onto the surface of the skin. It serves to increase the effect of the medicine serving for therapeutical purposes or to accelerate the penetration thereof or that of lack and/or trace elements or in a given case the effect of the active ingredient of some known pharmaceutical agent of the electrochemical processes already mentioned and to control the biological processes of the body in a natural way and promoted by a metallic substance according to the invention. In case, if only one or more metallic substances are used, the antispasmatic effect will be achieved based on the micro-currents obtained by the metallic elements having been affixed to the skin.

From the point of view of the invention all the elements, their mixtures, alloys or compounds thereof are considered as metallic substances, which are able to react electrolytically with the perspiration formed on the skin surface. The elements should not be toxic for the human organism. The elements having a higher electrolytic potential are the most advantageous ones, e.g. metals, preferably noble metals, copper, tin, zinc, maganese, molybdenum, cobalt, iron, magnesium, and alloys; further arsenic, bismuth, radium, selenium and the like. Naturally, these metals are to be provided in a quantity which is tolerable for the human organism.

The substances can be powdered. The size of the particles is not critical. The only requirement imposed is that the particles should not injure the skin surface. Metal plates, wires and the like can be arranged in any desired geometric configuration and metal-fibers, metal cloth and foils can be equally used. In particular, with noble metals it seems to be advantageous not to use a powder, since in such case the metal can be reclaimed and repeatedly be used. Preferably sulphur or a substance yielding sulphur ions, iodine or other deficiency elements are used as deficiency, lack and/or trace elements. I.e. some lack and/or trace elements among the metals enumerated can be called mineral vitamines.

For example, carbon mono- or dioxide, sulphur dioxyde, or a mixture thereof can be used.

According to a preferred embodiment of the process according to the invention the substances are applied onto the carrier in such a manner that freely adherent edge strips are left, thereafter the part of the carrier carrying the metallic substance and/or the lack and/or trace elements is covered with a thin protective layer, e.g. a thin grease-proof paper or a synthetic layer, which layer is to be removed by means of the adhesive edge strips in course of use.

There is furnished a process for preparing antispasmatic products, to be fixed on the skin, where onto some carrier surface or mixed with mud one or more kinds of metal or metallic substances and/or lack and/or trace elements and/or the pharmaceutical agent itself and in a given case the active ingredients of some known medicament is applied. The lack and/or trace element and in a given case the active ingredient of the known medicament being present are applied in form of a powder, a liquid or in gaseous form, while the powdered liquid and gaseous substances are placed into a recipient, e.g. a bag with a permeable wall onto the carrier, expediently on the margins of the carrier adhesive strip formed, while the substances on the carrier are covered with a removable protective layer and if required, prior to the application of the product to the skin it can be pretreated with a weak base or acid. A lack and/or deficiency element is present where the human body needs said element in an amount larger than provided in the food intake.

An adhesive plaster can be used as a carrier provided, in case of necessity, with an adhesive being neutral from the point of view of skin allergy.

The adhesive tape can be of the surgical type. Preferably, the tape can have a rubber based adhesive or an acrylate adhesive attached. The adhesive tape can be woven or nonwoven fabric.

Protectives can be employed to cover a dressing prepared with the active metal ingredients according to the present invention. Absorbent gauze can also be employed to support the active metal materials. Other support materials include oxidized cellulose, gauze bandage, purified cotton, and absorbent gauze. The active metal ingredients can also be incorporated into creams, dressings, glycerogelatins, pastes, an plasters, however, the upper-layer, contacting the skin, must be pure metallic.

Metal powder or filings or wires or plates having been arranged in any configuration can be used as a metal substance. A lack and/or trace element can be applied onto the carrier surface in form of a powder or as grains. Metallic substance and lack and/or trace elements can also be applied onto the carrier surface. Noble metals, copper, zinc, manganese, cobalt, molybdenum, selenium, iron and alloys can be used as a metallic substance. Sulphur, arsenic, bismuth, radium iodine or substances yielding sulphur ions or iodine ions, nontoxic materials being unharmful for the skin are applied onto the carrier as lack, deficiency and/or trace elements. Carbon dioxyde or a liquid active ingredient can be applied onto the carrier in a bag with permeable walls. A carrier, preferably with plaster or mixed iwth mud, a metallic substance and/or lack and/or trace element and/or pharmaceutical agent can be applied for mainly rheumatic and spasmolytic diseases. The pharmaceutical agent and/or metallic substance and/or lack and/or trace element can be used in an amount of 0,01 to 5,0 gram per square decimeter adhesive tape.

It is well known from the technical literature dealing with electrical work safety that under the influence of an alternating current the muscles of the human body become spasmatic on the places having been subjected to the influence of the current, and the person who suffered the accident, depending on his or her individual sensitivity and external circumstances, may be unable to control consciously his or her motions above a current intensity of 5 mA. In the technical literature various data and descriptions of experiments relating to this are to be found.

It becomes obvious from the technical literature dealing with the prevention of accidents that in course of accidents having been suffered with a direct current the muscles of the person, to whom the accident happened, become fully relaxed. When applying the product having been produced by means of the process according to the invention, this latter effect is utilized.

In course of the experiment it could be demonstated that even the weakest currents having been generated on the skin surface by means of the metallic substances applied onto said carrier are able to relax the spasm of the muscles and to introduce the lack and/or trace elements.

Accordingly, the invention is based on the recognition, that where a metallic substance is applied onto the skin surface at the location of the spasm of the muscle, a rather weak electrolytical direct current will be induced around the grains of the metallic substance and the metallic substance under the influence of a continuously forming perspiration on the contact service between the metallic substance having been applied to the skin and the induced electrolytic direct current substance penetrates under the skin and so in to the muscles. This effect can be increased by using an electolyte such as a weak base or acid.

The natural bio-currents having been formed in such electrolytic manner are exerting different influences.

The perspiration on the skin surface, which functions as an electrolyte between the grains of said metallic substance, generates an electrolytic current based on the small acidic or basic reaction of the perspiration, which behaves as an electolyte and which current penetrates under the skin surface into the muscles lying underneath and affects the nerve-paths, too. Depending on the conductivity of the body and in analogy to the effect of the direct current the penetrating electrolytic current causes the relaxation of the muscles under the adhesive tape.

Preferably an adhesive plaster is to be used as a carrier, since the perspiration does not easily evaporate from the covered skin surface, and as a consequence, efficiency can be increased.

When required, the electrolytic effects can be increased by means of a weak base or acid in such a manner that it is applied onto the carrier prior to the application thereof onto the surface of the skin. It goes without saying that only weak bases and acids not irritating or damaging the skin can be used for this purpose. It has been proved on several occasions that the spasm of the muscle relaxed already at the moment of the application of the product and within some minutes the spasm could be essentially stopped, or alleviated.

An effect similar to that of the acupuncture can be expected based on the assumption that the process is similar to acupuncture, in so far as the said metals with the known effect or the above metals are placed at the body locations known from acupuncture, that is onto the centres of higher potentials on the skin surface, or the place of the pain. Preferably an adhesive tape is used, however in this case the treatment is free from pain and neither the skin surface nor the deeper lying layers are injured.

Also in case of the acupuncture the metal needles planted into the skin generate an electrolytic potential with the fluids of the cells, the blood and other fluids. The current is led onto the nerve-paths. Probably, current generation in this case is more efficient, as there is more electrolyte present. However, acupuncture and conventional treatment of a patient can take place only in the presence of the physician, while when using the product according to the invention the product can be kept on the skin for a longer period, even for weeks, without injuring the skin although the extent of the electrolytic current is less than that associated with the acupuncture. In such a manner the effect can be increased to the multiple of the effect having been reached with acupuncture.

In the different points of the body simultaneously several metallic substances differing from each other and lack and/or trace elements can be applied in accordance with the invention. Depending on the metals applied to certain locations, different effects may be obtained.

Similarly to the process taking place with the acupuncture it can be assumed, that based on the electrolytic process some ions of the metallic substance or the lack and/or trace elements having been applied onto the skin surface penetrate into certain preselected or "aimed" places of the body due to the micro-currents and the potentials and change partly and to a certain extent the bio-currents. That is, trace elements or the ions thereof arrive at certain places. In such a manner healing can be attributed in both cases to the introduction of the lack and/or trace elements.

By means of the device having been produced in accordance with the invention, essentially three effects can be achieved:

1. The materials powder, liquid or gas, after having been applied onto the skin surface, are able to penetrate by diffusion, through the skin surface into the cells, i.e. through the pores thereof, by means of the adhesive plaster.

2. On the area with the plaster or adhesive tape surface the skin is not exposed to the air. Perspiration is formed, which together with the substance applied and the cell fluids induces an osmotic pressure.

3. It is quite obvious that even in the course of the osmosis between the membrane, that is the cell wall, and the two different fluids of the perspiration and the substances contained therein and of the cell fluids, a small potential difference will arise, enhancing the ion exchange between the two liquids through the cell wall.

Probably these currents are influencing to a certain extent the currents affecting the nerve-paths, too, and promote the delivery of the material particles into the deeper tissues. In case of lack and/or trace elements, or in a given case of the active ingredients of known pharmaceutical agents, the effect thereof can be increased, if the powder, liquid or gas or pharmaceutical agent to be introduced under the skin surface and applied onto the carrier are used together with metal particles which are able to produce a higher differential potential together with the perspiration and to accelerate in such a manner the introduction of the substance under the skin. Simultaneously, under the influence of the arising electrolytic current the previously mentioned muscle spasm relaxing effect also occurs, therefore in addition to the introduction of the lack and/or trace elements it becomes possible to relieve pains.

Naturally only such substances may be applied which are compatible with the substances or pharmaceutical agents to be introduced and which do not form toxic compounds therewith.

It goes without saying that efficiency of the treatment by using the product of the process according to the invention will be influenced by the size of the contacting surfaces, the pressure of contact, the duration of contact, the temperature, the properties and quantity of the materials applied and the quantity of the perspiration formed.

The product can be applied in cases, where the disease is caused by the absence of some chemical element and trace and/or lack element respectively, as well as in cases, in which spasms of the muscles occur such as rheumatism, tendovaginitis, locomotor disorders, muscle spasms resulting of sporting phlebitis, dyscopathia, spondylosis, lumbago, humeroscapular periarthritis, contusio, ischialgia, pains connected with scolosis, arthrosis generalis, cochsarthrosis, myalgia, Bechterew's disease, gout, tortykolis, decreasing of the mucous bursa after tendovaginitis, trigeminal neuralgia, tunnel syndroma, neuralgia postherpetica, generally in case of pains in the bones, muscles and where central and peripheral nerve pains occur. By proper use of the present product acupuncture can also be replaced, compare for example: Johannes Bischko, "Einführung in die Akupunktur", Haug Verlag, 4th Edition, Heidelberg, 1970.

The products of the invention may also be applied against headache, migraine, diseases of the throat, nose and ear, rhinitis, tinnitus, trigeminal neuralgia, geniculate neuralgia, vertigo, eye therapy, psychic diseases, sexual disturbances, psychic instability, insomnia, spastic diseases, metabolic disturbances, allergic diseases, toothache, intercostal neuralgia, etc. Compare for example Johannes Bischko, l.c., pages 51 to 75.

In many cases the effectiveness of the product of the invention could be proved in smaller or greater or in very small degree when the adhesive tape or plaster, with the above substances, lack or trace elements or with the mixture thereof, was fixed on the places indicated in the acupuncture praxis. The following effects were e.g. observed:

When the adhesive tape is placed in the inner hollow under the ankle after ca. 20 minutes a restful sleep may be ensured. At the same time within 10 minutes the pulse rate will be decreased by 4 to 6. This effect may be used e.g. for alleviating the rapid or anomalous heart action.

In case of biliary colic the literature, the book of Johannes Bischko mentioned above gives many references. During the experiments it has been stated that for achieving the effect the plaster should be fixed under the right second rib, a few square centimeter of the plaster is already enough. In this case after a maximum of 24 hours the bile will be discharged and the normal function thereof occurs.

Also many references are indicated against rhinitis or for palliation thereof. From among these references, a few square centimeters bridging of the joints of the thumb on side of the palm and the upper part of the hand proved to be effective. During the autumn epidemic of rhinitis the course of the disease subsided and the unpleasant last yellow discharge phase could be eliminated by the use of the product of the invention.

When the plaster was fixed on the inside blood vessel of the joint, the blood pressure was increased by 10 to 30 Torr.

The effect indicated in the literature occurred using the 358 acupuncture point less or more intensively.

For the spasm of the muscles the result to be expected was proved, i.e. the product of the invention is effective not only on the striated skeletal muscles but also stops the spasms of the smooth muscles, e.g. the biliary colic mentioned in the acupuncture, as well as the spasms of the stomach, intestine, the menstrual spasms and it is effective in case of myocardial and asthmatic spasms.

In view of the above described, the product of the invention delays the labour spasms when this is necessary e.g. owing to transportation or other reasons. After removing the plaster the spasms occur again.

In case of operated veins the pain at the location of the pain and the swelling may be stopped and the swelling may be decreased within 3 or 4 hours after applying the product of the invention.

Using the products of the invention many substances, which cannot be administered or can be administered only with difficulties through the alimentary system or in form of injections, may be administered without adverse side effects. So e.g. iron in case of anemia, selenium for the prevention of cardiac infarction as well as the five metallic vitamins, where many diseases occur in their absence or in the presence of only small amounts, may be administered. Without the metallic vitamins the organism may not produce the prophylactic substances, since the above metallic vitamins are catalysts for obtaining prophylactic substances, antibodies, vitamins, hormones, etc. The use of the products of the invention makes possible the prophylaxy and recovery from many diseases by using many substances and the combination thereof.

Experiments were performed for treating rheumatism and spasm of the muscle.

The plasters were measured in empty state and when treated with the active substance. Bands of 5 mm were left free on the edge of the plasters, so only a band of 10 cm×5 cm i.e. 0.5 square decimeter was sprinkled with the active substance. The active substance per square decimeter is stated in the last column.

The amount of the active ingredient is not important, it may be 0,01 to 5,0 gram per square decimeter, preferably 0,05 to 0,6 gram per square decimeter, most preferably 0,01 to 0,1 gram per square decimeter.

The rheumatic plaster is pressed onto the skin for ca. 30 sec. after having been fixed thereon.

The results are summarized as follows:

Rheumatic plaster

| Sample No. | Empty weight | Brutto weight | Weight of the active ingredient /Cu + S/ | |
|---|---|---|---|---|
| | | | gram | gram per square decimeter |
| 1. | 1.86 | 1.95 | 0.09 | 0.18 |
| 2. | 1.86 | 1.98 | 0.12 | 0.24 |
| 3. | 1.88 | 2.00 | 0.12 | 0.24 |
| 4. | 1.89 | 2.02 | 0.13 | 0.26 |
| 5. | 1.85 | 1.98 | 0.13 | 0.26 |
| 6. | 1.95 | 2.09 | 0.14 | 0.28 |
| 7. | 1.93 | 2.10 | 0.17 | 0.34 |
| 8. | 1.91 | 2.11 | 0.20 | 0.40 |
| 9. | 1.81 | 2.02 | 0.21 | 0.42 |
| 10. | 1.89 | 2.18 | 0.29 | 0.58 |

Plaster for stopping the spasm of the muscle

| Sample No. | Empty weight | Brutto weight | Weight of the active ingredients /Cu/ | |
|---|---|---|---|---|
| | | | gram | gram per square decimeter |
| 1. | 1.88 | 1.885 | 0.005 | 0.01 |
| 2. | 1.90 | 1.91 | 0.01 | 0.02 |
| 3. | 1.88 | 1.90 | 0.02 | 0.04 |
| 4. | 1.87 | 1.90 | 0.03 | 0.06 |
| 5. | 1.89 | 1.92 | 0.03 | 0.06 |
| 6. | 1.85 | 1.88 | 0.03 | 0.06 |
| 7. | 1.88 | 1.91 | 0.03 | 0.06 |
| 8. | 1.82 | 1.85 | 0.03 | 0.06 |
| 9. | 1.90 | 1.94 | 0.04 | 0.08 |
| 10. | 1.81 | 1.82 | 0.07 | 0.14 |

After the above treating the pain may relapse. In this case only a plaster of 0,5 cm×0.5 cm or that of 1 square centimeter should be placed onto the point of pain, and the pain will be eliminated.

The following tables show the results of the clinical examinations. Using other types of the plaster the side effects indicated do not appear.

| EXPERIMENTS WITH PLASTERS STOPPING THE SPASM OF THE MUSCLE | | | | | | |
|---|---|---|---|---|---|---|
| Diagnosis | Number of the cases | Complaints unchanged | subsided | stopped | Time of observing the effect | |
| myalgia | 24 | 3 | 7 | 14 | 10 min to 3 days | 4 dermatitis |
| discopathia | 4 | 2 | 1 | 1 | from 7th day | 1 dermatitis |
| Spondylosis cervicalis | 8 | 2 | 4 | 2 | 30 min. to 4 days | 3 dermatitis 1 itching |
| Lumbago | 5 | — | 3 | 2 | 6 to 24 hours to 9 days | — |
| Periarthritis humero scapularis | 4 | 1 | 2 | 1 | 24 hours to 8 days | 1 dermatitis |
| Tendovaginitis | 3 | — | 1 | 2 | 4 hours to 6 days | 1 dermatitis |
| Ischialgia | 3 | 1 | 1 | 1 | 2 hours to 5 days | — |
| Contusio | 3 | — | 2 | 1 | 30–60 min. | — |
| Scoliosis | 2 | — | 1 | 1 | from 7th day | — |
| Arthrotis gen. | 1 | — | 1 | — | — | — |
| Total | 57 | 9 | 23 | 25 | | 11 |
| % | 100 | 15,8 | 40,3 | 43,9 | | 19,3 |
| | | | | 84,2 | | |

| EXPERIMENTS WITH RHEUMATIC PLASTERS (CU + S = 1:2 parts by weight) | | | | | | |
|---|---|---|---|---|---|---|
| Diagnosis | Number of the cases | Complaints unchanged | subsided | stopped | Time of occuring the effects | Side effects |
| myalgia | 10 | 2 | 2 | 6 | 24 hours–7 days | 4 dermatitis |
| Arthrosis gen | 1 | 1 | | | | |
| Tendovaginitis | 2 | — | 2 | | from 6th day | 1 dermatitis |
| Coxarthrosis | 1 | — | 1 | — | 24 hours | — |
| Contusio | 1 | — | 1 | — | 3 days | 1 dermatitis |
| Discopathia | 2 | 1 | 1 | — | 24 hours | 1 dermatitis |
| Lumbago | 2 | 1 | — | 1 | 9 days | — |
| Periarthritis humero scapularis | 2 | 1 | 1 | — | 24 hours | 1 dermatitis |
| Spondilosis cervicalis | 3 | 1 | 1 | 1 | from 8th day | 1 dermatitis |
| other | 2 | — | 2 | — | 3–5 days | 1 dermatitis |
| Total | 26 | 7 | 11 | 8 | | 10 dermatitis |
| % | 100 | 26,9 | 42,3 | 30,8 | | 38,5 |
| | | | | 73,1 % | | |

It will be understood that each of the elements described above, or two or more together, may also find a useful application in other types of bandage system configurations and skin treatment procedures differing from the types described above.

While the invention has been illustrated and described as embodied in the context of externally applied antispasmatic products, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art; fairly constitute essential characteristics of the generic or specific aspects of this invention.

What is claimed as new and desired to be protected by Letters Patent is set forth in the appended claims:

1. A method for providing pharmaceutical skin contacting products suitable for originating weak currents between active ingredient and perspiration of the skin comprising
   preparing a carrier for supporting material containing an active metal ingredient;
   disposing a material containing an active metal ingredient at the carrier; and
   furnishing an attachment mechanism for bringing the material containing an active metal ingredient into close contact with the skin of the human body.
2. A method for providing pharmaceutical skin contacting products according to claim 1 wherein the carrier is a member selected from the group consisting of clay, mud, cream, paste, plaster, dressing, jelly, cotton, gauze, sponge, napkin, pad, bandage, adhesive tape, adhesive and mixtures thereof, providing that the upper layer of the active ingredient contacting the skin is pure metallic.

3. A method for providing pharmaceutical skin contacting products according to claim 1 wherein the active metal ingredient is provided by a non-toxic member selected from the group consisting of metal powder, metal filings, wires, fibers, metal fabric, metal strips, metal platelets, metal crystals, metal sponge, metal grain and mixtures thereof.

4. A method for providing pharmaceutical skin contacting products according to claim 1 wherein the material containing an active metal ingredient further comprises an element selected from the group consisting of sulphur, bismuth, radium, tellurium, iodine, arsenic, antimony and mixtures thereof.

5. A method for providing pharmaceutical skin contacting products according to claim 1 wherein the active metal ingredient contains a member selected from the group consisting of noble metals, copper, zinc, tin, manganese, cobalt, molybdenum, iron, arsenic, selenium, alloys thereof and mixtures thereof.

6. A method for providing pharmaceutical skin contacting products according to claim 1 further comprising applying a fluid medium to the carrier via a permeable bag containing said fluid medium.

7. A method for providing pharmaceutical skin contacting products according to claim 1 further comprising applying the pharmaceutical skin contacting product to human skin based on an adhesive support area mechanically adhering to the skin.

8. A method for providing pharmaceutical skin contacting products according to claim 1 wherein the active metallic ingredient is employed in an amount of from about 0.01 to 5.0 g per square decimeter adhesive tape.

9. A method for providing pharmaceutical skin contacting products according to claim 1 further comprising pretreating the carrier before applying on the skin with an electrolyte generating an aqueous solution with a pH in the range of from about 5 to 9.

10. A pharmaceutical skin contacting product comprising
   a material containing an active metal ingredient;
   a carrier for supporting material containing the active metal ingredient;
   means for attaching the carrier supporting an active metal ingredient to the skin of the human body for providing close contact between the active metal ingredient and the skin for originating weak currents between the active metal ingredient and the perspiration of the skin, where the perspiration acts like an electrolyte.

11. The pharmaceutical skin contacting product according to claim 10 wherein the carrier is a member selected from the group consisting of clay, mud, cream, paste, plaster, dressing, jelly, cotton gauze, sponge, napkin, pad, bandage, adhesive tape, adhesive and mixtures thereof, providing that the upper layer of the active ingredient contacting to the skin should be pure metallic.

12. The pharmaceutical skin contacting product according to claim 10 wherein the active metal ingredient is provided by a nontoxic member selected from the group consisting of metal powder, metal filings, wires, fibers, metal fabric, metal strips, metal platelets, metal crystals, metal sponge, metal grain and mixtures thereof.

13. The pharmaceutical skin contacting product according to claim 10 wherein the material containing an active metal ingredient further comprises an element selected from the group consisting of sulphur, tellurium, iodine, arsenic, bismuth, radium, antimony and mixtures thereof.

14. The pharmaceutical skin contacting product according to claim 10 wherein the active metal ingredient contains a member selected from the group consisting of noble metals, copper, zinc, tin, manganese, cobalt, molybdenum, iron, arsenic, selenium, alloys thereof and mixtures thereof.

15. The pharmaceutical skin contacting product according to claim 10 further comprising a permeable bag containing a fluid medium for applying the fluid medium to the carrier.

16. The pharmaceutical skin contacting product according to claim 10 further comprising an adhesive support area for mechanically adhering to the skin for applying the pharmaceutical skin contacting product to human skin.

17. The pharmaceutical skin contacting product according to claim 10 wherein the active metallic ingredient is employed in an amount of from about 0.01 to 5.0 g per square decimeter adhesive tape.

18. The pharmaceutical skin contacting product according to claim 10 wherein the means for attaching comprises a surgical adhesive tape with a coating of an acrylate adhesive.

19. The pharmaceutical skin contacting product according to claim 10 wherein the active metal ingredient is embedded in a carrier containing vinyl plastic, providing that the upper layer of the active ingredient contacting the skin is pure metallic.

20. The pharmaceutical skin contacting product according to claim 10 wherein the metal is copper and where the carrier comprises an adhesive tape where the edge zones around the copper material are provided with an ahesive coating for attachment to the human skin.

21. Process for preparing antispasmatic products for being be fixed on the skin comprising applying a substance of the group consisting of metal, metallic substances, deficiency material, trace element and mixtures thereof onto some carrier surface wherein the substance is applied in the form of a member selected from the group consisting of powder, liquid, gas and/or mixtures thereof providing on the margins of the carrier an adhesive strip; and
   covering the substances on the carrier with a removable protective layer.

22. A method for production of antispasmatic preparations for attachment to skin comprising placing on a surface of a carrier an active member selected from the group consisting of metals, metallic materials, trace elements, deficiency elements and mixtures thereof;
   placing adhesive material at edges of the surface of the carrier for providing a strip which can be adhesively attached to skin;
   placing a removable protective layer over the active member for originating weak currents between the active member and the perspiration of the skin, where the perspiration acts like an electrolyte.

23. The method for production of antispasmatic preparations for attachment to skin according to claim 22 further comprising pretreating the carrier before application to human skin by applying a fluid medium to the carrier, where the fluid medium is an electrolytic aqueous solution with a pH in the range of from about 5 to 9.

24. The method for production of antispasmatic preparations for attachment to skin according to claim 22 further comprising placing an adhesive support area on a carrier base material to provide a carrier mechanically adhering to skin, where the adhesive support area is pharmaceutically compatible with human skin.

25. The method for production of antispasmatic preparations for attachment to skin according to claim 22 further comprising employing a member selected from the group consisting of metal powders, file dust, wires, plates, foils, metal fiber, metal grid or mixtures thereof as an active member.

26. The method for production of antispasmatic preparations for attachment to skin according to claim 22 further comprising placing deficiency elements and/or trace elements onto the carrier as a granular powder material.

27. The method for production of antispasmatic preparations for attachment to skin according to claim 22 further comprising employing a member selected from the group consisting of copper, zinc, tin, manganese, cobalt, molybdenum, iron, arsenic, bismuth, radium, alloys thereof and mixtures thereof as an active member.

28. The method for production of antispasmatic preparations for attachment to skin according to claim 22 further comprising placing a member selected from the group consisting of iodine, sulphur, iodine generating materials, sulphur generating materials and mixtures thereof as non-toxic materials onto the carrier, which do not damage skin.

29. The method for production of antispasmatic preparations for attachment to skin according to claim 22 further comprising employing the active member in an amount of from about 0.01 to 5 gram per square decimeter of carrier surface.

* * * * *

UNITED STATES PATENT AND TRADEMARK OFFICE
CERTIFICATE OF CORRECTION

PATENT NO.  : 4,755,384
DATED       : July 5, 1988
INVENTOR(S) : Otto Mallasz

It is certified that error appears in the above-identified patent and that said Letters Patent is hereby corrected as shown below:

Please insert in the patent as follows:

Title page, between (22) and (30)

--Related U.S. Application Data

(63) Continuation in part of PCT/HU83/00040, July 15, 1983, published as WO 84/00297, February 2, 1984.--

Signed and Sealed this

Second Day of May, 1989

*Attest:*

DONALD J. QUIGG

*Attesting Officer*     *Commissioner of Patents and Trademarks*